(12) United States Patent
Katz

(10) Patent No.: US 9,610,336 B1
(45) Date of Patent: Apr. 4, 2017

(54) IMMUNOTHERAPY FOR LYME DISEASE

(71) Applicant: Amiram Katz, Orange, CT (US)

(72) Inventor: Amiram Katz, Orange, CT (US)

( * ) Notice: Subject to any disclaimer, the term of this patent is extended or adjusted under 35 U.S.C. 154(b) by 0 days.

(21) Appl. No.: 14/799,553

(22) Filed: Jul. 14, 2015

Related U.S. Application Data

(60) Provisional application No. 62/025,051, filed on Jul. 16, 2014.

(51) Int. Cl.
| *A61K 39/02* | (2006.01) |
| *A61K 49/00* | (2006.01) |
| *A61K 39/395* | (2006.01) |
| *C07K 16/12* | (2006.01) |
| *A61K 39/00* | (2006.01) |

(52) U.S. Cl.
CPC ...... *A61K 39/0225* (2013.01); *C07K 16/1207* (2013.01); *A61K 2039/521* (2013.01); *C07K 2317/76* (2013.01)

(58) Field of Classification Search
USPC .. 424/9.1, 130.1, 141.1, 150.1, 184.1, 234.1
See application file for complete search history.

(56) References Cited

U.S. PATENT DOCUMENTS

| 5,582,829 A | * | 12/1996 | Alligier | C12N 13/00 424/234.1 |
| 5,780,030 A | * | 7/1998 | Simon | C12N 1/20 424/150.1 |
| 6,592,875 B1 | * | 7/2003 | McMichael | A61K 39/0225 424/184.1 |

OTHER PUBLICATIONS

Fikrig, E., et al. Infection and Immunity, vol. 60, No. 2, pp. 657-661, Feb. 1992.*
Barbour, A.G., et al. Infection and Immunity, vol. 52, Nol. 5, pp. 549-554, May 1986.*

* cited by examiner

*Primary Examiner* — Rodney P. Swartz
(74) *Attorney, Agent, or Firm* — Fattibene and Fattibene LLC; Paul A. Fattibene

(57) ABSTRACT

Diseases caused by a spirochete bacteria are treated. Doses of an anti-flagellin monoclonal antibody, spirochetal protein, or Lyme lysate are used in predetermined increasing doses to effectively treat diseases and symptoms caused by spirochete bacteria, and in particular Lyme disease.

7 Claims, 1 Drawing Sheet

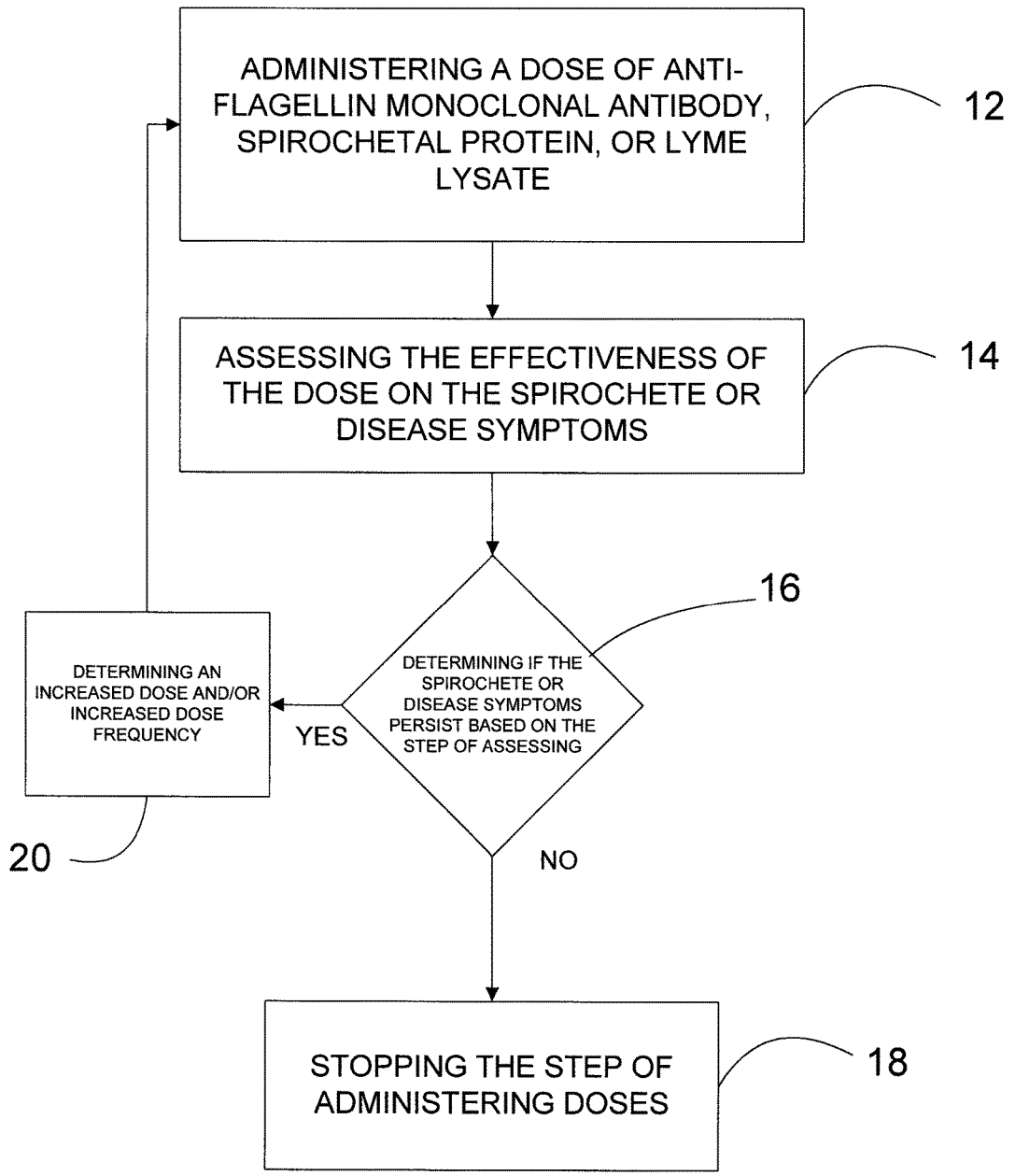

IMMUNOTHERAPY FOR LYME DISEASE

RELATED APPLICATION

This application claims the benefit of U.S. Provisional Application No. 62/025,051 filed Jul. 16, 2014.

FIELD OF THE INVENTION

The present invention relates in general to the treatment of Lyme disease, and more particularly to immunotherapy for treating Lyme disease.

BACKGROUND OF THE INVENTION

Lyme disease is a growing epidemic in the US. On August 18, at the 2013 International Conference on Lyme Borreliosis and Other Tick-Borne Diseases, the CDC (center of disease control) released new data on the number of people affected each year by Lyme disease. Namely, it pointed to a major difference in the recorded number of people affected by the disease and the actual number.

Upwards of 300,000 people appear to contract the disease annually, which is about 10 times what's typically reported to the CDC. Generally, there is a difference in the recorded and actual numbers of a given disease, but for Lyme disease there are many more than previously thought. Still, the new report is helpful in understanding the reality of how prevalent the disease is. Catching the disease early on is one key to treating it successfully. Reducing the raw numbers of people affected by the disease will take some comprehensive and collaborative efforts.

If not treated in a timely manner with antibiotics, which is hard to do if the typical "Bull's Eye" rash doesn't develop (the "Bull's Eye" rash does not develop in about 50% of the patients), the disease will progress into a chronic immuno-inflammatory condition, where antibiotics don't work. Even when caught early enough and treated adequately with antibiotics, 10% of the patients will develop an autoimmune condition resistant to antibiotic treatment.

Autoimmune and inflammatory conditions will not respond to antibiotics, unless they possess anti-inflammatory properties, like tetracyclines and macrolides, where the response will be limited.

There is a need for an effective, safe and inexpensive treatment of the chronic condition that develops after Lyme infection, known as "Post treatment Lyme disease", which is turning to be the pandemic of the 21st century.

SUMMARY OF THE INVENTION

The present invention provides a treatment for Lyme disease or other diseases caused by a spirochete bacteria using immunotherapy. In a first treatment monoclonal antibodies are used targeting the flagella protein so as to immobilize or paralyze the spirochete bacteria and to launch an immune attack on the spirochete bacteria. In a second treatment spirochetal proteins, such as outer surface proteins A (OspA) and outer surface proteins B (OspB) are administered parenterally or injected.

In both treatments the treatment will be done with gradually increasing incremental dosing.

Accordingly, it is an object of the present invention to treat Lyme disease, and especially advanced cases of Lyme disease.

It is an advantage of the present invention that advanced stages of Lyme disease can be effectively treated.

It is a feature of the present invention to provide increasing doses of a monoclonal antibody targeting the flagella portion of a spirochete bacteria, and specifically a *Borrelia* spirochete bacteria.

It is another feature of the present invention to provide parentral administration of increasing doses of a spirochetal protein, and specifically outer surface proteins.

These and other objects, advantages, and features will become more readily apparent in view of the following more detailed description.

BRIEF DESCRIPTION OF THE DRAWING

The FIGURE is a flowchart illustrating the method steps of the present invention.

DETAILED DESCRIPTION OF THE INVENTION

Treatment #1:
Anti-Flagellin Monoclonal Antibodies.

One of the reasons the immune system cannot handle the *Borrelia* spirochete effectively is its motion. The spirochete's motion is generated by the flagella, which are like propulsion tails, six to eight in number, that originate and are anchored at both tips of the spirochete, and consist of close to 20% of the spirochete's mass. At the tips of the body of the spirochete, is the "motor", that moves the flagella, that are in most part internal (between the plasma membrane and the cell wall). The flagella are not propelling the spirochete by serving as "oars", instead they change the shape of the spirochete and "swim" like a dolphin. It is not surprising that the most common band seen on the Lyme western blot test is 41, which are antibodies against the abundant flagella protein, which is of 41 kd size.

Producing monoclonal antibodies targeting the flagella protein and administering them to affected individuals at any stage of the infection will achieve two goals: FIRST, it will paralyze the spirochete and allow the immune system to deal with a more static target and SECOND, it will launch a massive immune attack on the spirochete resulting in its destruction.

After extensive in vitro studies utilizing live *B. burgdorferi* spirochetes and demonstrating the mechanisms of action of the monoclonal antibodies. Human trials will be conducted, where monoclonal antiflagellar antibodies will be administered at varying concentrations and frequencies of administration, until disease elimination is accomplished. To avoid an overwhelming "die off" response the treatment will be done with gradual incremental dosing.

Treatment #2:

Parenteral Administration of OspA (Outer Surface Proteins A), OspB (Outer Surface Proteins B), and Other Spirochetal Proteins (Including Sonified Borrellial Solution)

One of the theories explaining the morbidity associated with Lyme infection, especially the late disease, or "Post treatment Lyme disease" is that some of the spirochetal proteins have sections or segments of their structure which are similar to human proteins, including proteins of the nervous system.

The induction of autoimmunity due to protein "look alike" between the invader and the host is called "molecular mimicry". Because the similarity also leads to evasion of the spirochete from our immune system, any time we face a scenario of autoimmunity by molecular mimicry, we will probably encounter an evolutionary step leading to natural selection of the mutated, now "mimicking" protein of the microorganism, which can now survive (persist) in the host without the typical infectious course, but may elicit an ongoing inflammatory, or an autoimmune response.

In summary, the results of "molecular mimicry" is that the immune system may fail to identify the spirochete as foreign (non self), because of mimicry (protein similarity achieved through "natural selection"); and at the same time fails to identify some of the human proteins as "self" and starts attacking them.

Since our "mimicked" proteins, now treated as non self, will continue to fuel an on-going autoimmune response, the only theoretical way to stop it apart of general measures of immune modulation/suppression is to "feed" the immune system with the origin of the mimicry—the spirochetal proteins which initiated this autoimmune process.

After in vitro studies showing interaction of immune cells/immunoglobulins obtained from patients with a typical post infectious autoimmune syndrome and spirochetal proteins, human trials utilizing increasing concentrations of spirochetal proteins will follow.

To avoid an overwhelming "Herxheimer's reaction", the treatment will be done with gradual incremental dosing of the spirochetal proteins.

e.g. (including but not limited to), initial 3 ng of LymeRix OspA (10%). LymeRix is a trademark for a recombinant vaccine against Lyme disease based on the outer surface protein A or OspA of *Borrellia burgdorferi* developed by SmithKline Beecham. It will be preferable to obtain the Pasteur Merleux Connaught ImuLyme for this purpose, because it is a nonadjuvanted preparation. ImuLyme is a trademark for a recombinant outer surface protein A vaccine developed by Aventis Pasteur, Inc. We want to block receptors, rather than initiate an immune response. This vaccine was tried in parallel to the Lymerix, but due to competition and market analysis, the company never requested an FDA clearance to pursue the American market.

Initially, the dose will preferably begin at a 1/100 or 1% concentration and increase gradually to a higher concentration. The administering of the gradually increasing dose may occur of a predetermined time that is therapeutically effective.

Also, in addition to the proteins, a spirochete or Lyme lysate may be used. A Lyme lysate is a fluid containing the contents of a lysed cell from a bacteria causing Lyme disease, such as the *Borrelia* spirochete. Lysis occurs when there is a breakdown of the cell that compromises its integrity.

The term dose may relate to a quantity of medicament or agent for treating a disease and/or the frequency of administering the medicament or agent for treating a disease.

The FIGURE illustrates a method of treating Lyme disease according to the present invention. Box 12 represents the step of administering a dose of anti-flagellin monoclonal antibody, spirochetal protein, or spirochetal or Lyme lysate to a patient. Box 14 represents the step of assessing the effectiveness of the dose on the spirochete or disease symptoms. Diamond shaped box 16 represents the step of determining if the spirochete or disease symptoms persist based on the step of assessing represented by box 14. If there is no longer any detection of a spirochete or the disease symptoms no longer persist then the step of stopping the step of administering doses is performed, as represented by box 18. However, if the spirochete or disease symptoms persist than the step of determining an increased dose and/or increased dose frequency is performed, as represented by box 20, and the step of administering a dose is repeated, as illustrated by box 12. The step of determining an increased dose and/or increased dose frequency, as represented by box 20, is repeated as long as said step of determining if the spirochete or disease symptoms persists results in a positive or yes determination. As a result of this iterative process the disease caused by the spirochete, and in particular Lyme disease, is successfully treated.

While the present invention has been described with respect to several different embodiments, it will be obvious that various modifications may be made without departing from the spirit and scope of this invention.

What is claimed is:

1. A method of treating Lyme disease comprising the step of:

administration of a dose of monoclonal antibodies targeting the 41 kd flagellar protein of *B. burgdorferi;* repeating said step of administration of a dose of monoclonal antibodies targeting the 41 kd flagellar protein of *B. burgdorferi* at variable intervals;

determining if Lyme disease symptoms persist;

increasing the dose after each said step of administration of a dose of monoclonal antibodies targeting the 41 kd flagellar protein of *B. burgdorferi* as long as the Lyme disease symptoms are determined to persist in said step of determining if Lyme disease symptoms persist.

2. A method of treating Lyme disease comprising the steps of:

administering an initial dose of 3 ng and a series of increasing doses of spirochetal proteins including a non-adjuvant recombinant vaccine based on an outer surface protein A of *Borrelia burgdorferi* as long as Lyme disease symptoms persist.

3. A method of treating Lyme disease comprising the step of:

administering lysed cells from a bacteria causing Lyme disease in increasing doses as long as Lyme disease symptoms persist.

4. A method of treating a disease caused by a spirochete in a patient comprising the steps of:

administering a dose selected from the group consisting of an anti-spirochete flagellin monoclonal antibody, a spirochetal protein, and a spirochete lysate;

assessing the effectiveness of the dose on the spirochete or disease symptoms;

determining if the spirochete or disease symptoms persist based on the step of assessing;

increasing the dose in said step of administrating a dose as long as the step of determining if the spirochete or disease symptoms persist; and stopping said step of administering a dose when said step of determining if the spirochete or disease symptoms persist, whereby a disease caused by a spirochete is capable of being successfully treated.

5. A method of treating a Lyme disease caused by a *Borrelia burgdorferi* in a patient comprising the steps of:

administering a dose selected from the group consisting of an anti-flagellin monoclonal antibody of *Borrelia burgdorferi*, and a protein of *Borrelia burgdorferi;* assessing the effectiveness of the dose on the *Borrelia burgdorferi* or disease symptoms;

determining if the *Borrelia burgdorferi* or disease symptoms persist based on the step of assessing;

increasing the dose in said step of administrating a dose as long as the step of determining if the *Borrelia burgdorferi* or disease symptoms persist; and stopping said step of administering a dose when said step of determining if the *Borrelia burgdorferi* or disease symptoms persist, whereby a disease caused by the *Borrelia burgdorferi* is capable of being successfully treated.

6. A method of treating a Lyme disease caused by a *Borrelia burgdorferi* in a patient as in claim 5 wherein:
   said step of administering a dose comprises a dose of 3 ng or greater of a protein of *Borrelia burgdorferi*.

7. A method of treating Lyme disease comprising the step of:
   administering monoclonal antibodies targeting flagellar protein of *Borrelia burgdorferi* in increasing doses as long as Lyme disease symptoms persist.

* * * * *